United States Patent [19]

Stern

[11] 4,144,347

[45] Mar. 13, 1979

[54] 3-(N-IMIDAZOLYL)-2-NITROBENZOFU-RANS

[75] Inventor: Richard M. Stern, Cottage Grove, Minn.

[73] Assignee: Riker Laboratories, Inc., Northridge, Calif.

[21] Appl. No.: 919,413

[22] Filed: Jun. 26, 1978

[51] Int. Cl.$^2$ .................. A61K 31/415; C07D 405/04
[52] U.S. Cl. .................................. 424/273 R; 548/336
[58] Field of Search ..................... 548/336; 424/273 R

[56] References Cited

U.S. PATENT DOCUMENTS

| 3,927,018 | 12/1975 | Houlihan | 548/336 |
| 4,012,414 | 3/1977 | Pelosi | 548/336 |

OTHER PUBLICATIONS

Areschka et al., Chem. Abst. 1972, vol. 77, No. 164591j.
Chem. Abst. vol. 83, Chemical Substance Index, I–Ph, Jul.–Dec. 1975, p. 2693CS, the first col. 4th entry from the bottom.
Eloy et al., Chem. Abst. 1975, vol. 83, No. 9907x.
Kempter et al., Chem. Abst. 1969, vol. 70, No. 11630b.

*Primary Examiner*—Natalie Trousof
*Attorney, Agent, or Firm*—Cruzan Alexander; Donald M. Sell; Donald C. Gipple

[57] ABSTRACT

3-(N-Imidazolyl)-2-nitrobenzofurans, optionally substituted on the benzo ring, which are active as antimicrobial agents and processes for their use.

4 Claims, No Drawings

3-(N-IMIDAZOLYL)-2-NITROBENZOFURANS

BACKGROUND OF THE INVENTION

This invention relates to simple halogen, methyl, ethyl and methoxy substituted 3-(N-imidazolyl)-2-nitrobenzofurans, and to the use of these compounds as antimicrobial agents.

Although various 2-nitrobenzofurans have been reported in recent years and are known to the art, compounds which contain both an imidazole ring and a benzofuran ring, with or without a nitro group, have not been disclosed heretofore. More particularly, compounds of the type covered by the present invention, i.e. wherein 2-nitrobenzofuran is substituted in the 3-position by an N-imidazolyl ring are completely unknown.

DETAILED DESCRIPTION OF THE INVENTION

The present invention relates to 3-(N-imidazolyl)-2-nitrobenzofurans, optionally substituted on the benzo ring, which are active as antimicrobial agents. It also relates to the use of the compounds as antimicrobial agents.

According to the present invention, there is provided a class of compounds of the formula

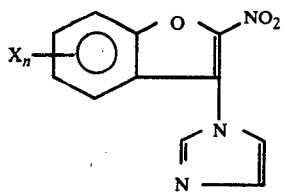

wherein X is halogen, methyl, ethyl or methoxy and n is zero or one, or when X is methyl or methoxy, n can also be two. When n is zero, the benzo ring is unsubstituted. Halogen herein (in X) is preferably fluorine, chlorine or bromine, most preferably chlorine.

The pure compounds of the invention are generally white or yellow crystalline solids which are insoluble in water and hydrocarbons and are more soluble in acetone, lower alkanols, N,N-dimethylformamide and the like.

All of the compounds of the invention are active against bacteria and some are also active against other microorganisms, including fungi and protozoa, in vitro and topically. Thus, they can be used for disinfecting and sterilizing, for example of medical and dental equipment, as components of disinfecting solutions. The compounds are particularly useful as antibacterial agents.

The compounds of the invention are prepared by several methods, either directly from starting materials known to the art, or from intermediates which are prepared by methods well known to the art. Thus, 3-bromobenzofuran, which is a major intermediate in the preparation of the compounds I, is a known compound and is conveniently prepared from benzofuran by 2,3-dibromination with bromine followed by dehydrobromination with strong base such as potassium hydroxide, which provides 3-bromobenzofuran. This synthetic method is also generally applied to suitably substituted benzofurans to provide intermediate benzo-substituted 3-bromobenzofurans. The reaction sequence beginning with these compounds can be represented as follows:

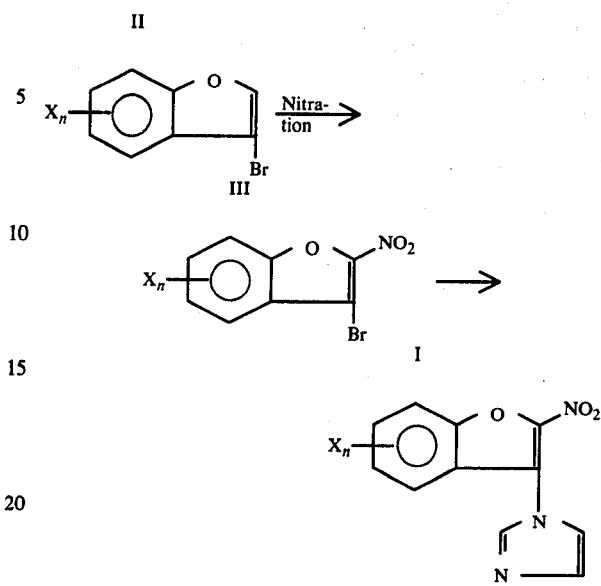

wherein X and n are as previously indicated.

The intermediates of formula II are converted to intermediates of formula III preferably by direct nitration with dinitrogen tetraoxide, although nitration with a mixture of nitric acid and sodium nitrite can also be used. Nitration with dinitrogen tetraoxide is effected with or without an inert solvent, but preferably without solvent, at moderate temperatures from about 0° to 100° C.

Compounds of formula I of the invention are prepared from compounds of formula III by reaction with an alkali metal salt of imidazole such as sodium imidazole (formed by the reaction of imidazole with a strong base such as sodium hydride). The 3-bromo group is readily displaced by the imidazole group in this reaction. The reaction is carried out in an inert solvent and preferably in an inert solvent which facilitates ionic reactions, such as an N,N-dialkyl amide of an organic acid, for example N,N-dimethylformamide. The temperatures used for the reaction are generally about 50°–150° C., although higher temperatures can be used if necessary.

The antimicrobial activity of the compounds is evaluated using a variation of the original agar-plate diffusion method of Vincent and Vincent (e.g. see Vincent, J. G., and Vincent, Helen W., Proc. Soc. Exptl. Biol. Med. 55: 162–164, 1944, and Davis, B. D., and Mingioli, E. S., J. Bac. 66: 129–136, 1953). Using this test, the compounds, of the invention have been found to have a broad spectrum of activity against both gram-positive and gram-negative microorganisms. The procedure provides information on the amount of a compound required to give complete inhibition, partial inhibition or no inhibition of microbial growth on agar plates. The microbial growth on each plate is read visually, and minimal inhibitory concentrations are recorded.

The microorganisms used are: *Staphylococcus aureus, Bacillus subtilus, Pseudomonas aeruginosa, Escherichi coli, Streptococcus sp.* (strains isolated from dental caries in rats or hamsters at the National Institute of Dental Health and grown in PFY or APT agar), *Asperigillus niger, Candida albicans, Mima polymorpha, Herellea vaginicola, Klebsiella pneumoniae* and *Streptococcus fecaelis.*

These are selected representatives of various bacterial and fungal classes, and broad spectrum activity can be predicted as a result of activity against them. All of the compounds of the invention possess antimicrobial activity towards one or more of them. The compounds maintain high activity against the microorganisms either in the absence or presence of 10 percent horse serum.

The in vivo antimicrobial activity is determined against infections produced by *Streptococcus pyogenes* C-203, and *Staphylococcus aureus* (Smith) or other bacterial species. The species used is determined by the in vitro antimicrobial spectrum of the compound. Groups of 5 or 10 mice, 18–22 g., are infected intraperitoneally with the test culture. Treatment consists of three oral injections one, six and 24 hours after infection. All mice are observed for extended periods, e.g. for two weeks and deaths recorded at daily intervals. Control groups consist of one infected, nontreated group and other infected groups receiving varying dosages of a reference standard.

The acute oral toxicity of the compounds of the invention generally is moderate to low compared with the effective oral dose, and they have a good to excellent therapeutic ratio.

The compounds of the invention may be formulated by incorporating them into conventional pharmaceutical carrier materials, either organic or inorganic, which are suitable for oral or intraperitoneal application. For in vitro or topical use, simple aqueous solutions or suspensions are most conveniently employed. For this purpose, concentrations of the order of 100 parts per million up to about 5 parts per thousand are suitable, and the formulation is used by immersing the object to be treated therein, or by local application to an infected area. The amount of compound to be used for treatment of a microbial infection will be an effective amount less than a toxic amount. The amount to be administered to a subject and route of administration to control an infection will depend on the species of organism, the sex, weight, physical condition of the subject, the locus of the infection, and many other factors, but this judgment is well within the skill of the art. Usually the amount will be less than 100 mg/kg per dose. Conveniently the oral treatment is administered in the form of the usual pharmaceutical preparation such as capsules, tablets, emulsions, solutions, suppositories and the like. Excipients, fillers, coatings, etc. are employed with tablets or capsules, as is well known in the art.

It is often advantageous to combine the compounds of this invention with other antimicrobial compounds such as coccidiostats, anthelmintics, antifungals, antibiotics, steroids, or antibacterial agents, or to combine more than one compound described herein in a single composition.

In view of the outstanding antimicrobial activity of the compounds, they would also be expected to be effective growth promoters in various animal and bird species.

The following examples are given for the purpose of illustrating some of the synthetic methods useful in the invention, but are not intended to limit the invention. The melting points are uncorrected and the temperatures are in degrees Centigrade.

EXAMPLE 1

A 5.0 g. sample of powdered 3-bromobenzofuran on a glass dish is placed next to a container of nitric acid. Sodium nitrite is added periodically to the nitric acid, and the entire experiment is covered with a bell jar. After about 15 minutes the powder becomes an oil. After 12 hours the product is dissolved in hot methanol and slowly crystallized by cooling. Recrystallization from methanol provides yellow crystals of 3-bromo-2-nitrobenzofuran, m.p. 130°–132° C. (lit. 132° C.).

| Analysis: | %C | %H | %N | %Br |
|---|---|---|---|---|
| Calculated for $C_8H_4BrNO_3$: | 39.6; | 1.7; | 5.8; | 33.0 |
| Found: | 39.5; | 1.7; | 5.6; | 32.9 |

EXAMPLE 2

To a stirred 80 g. sample of solid 3-bromobenzofuran is added a large excess of dinitrogen tetraoxide. The mixture liquifies within 5 minutes. After 2 hours, the mixture is triturated with ethanol and filtered to provide yellow crystals of 3-bromo-2-nitrobenzofuran. The product is identical to the product of Example 1 according to infrared spectral analysis.

EXAMPLE 3

To a stirred solution of 0.1 g. (12 mmole) of imidazole in 20 ml. of N,N-dimethylformamide is added 0.5 g. (12 mmole) of 57.6 percent suspension of sodium hydride in mineral oil. After cooling to 20° C., 2.4 g. (10 mmole) of 3-bromo-2-nitrobenzofuran in 20 ml. of N,N-dimethylformamide is added. After stirring 45 minutes, the mixture is heated on a steam bath for 15 minutes, then 50 ml. of water are added. Cooling and filtration provide yellow needles of 3-(N-imidazolyl)-2-nitrobenzofuran, m.p. 147°–149° C.

| Analysis: | %C | %H | %N |
|---|---|---|---|
| Calculated for $C_{11}H_7N_3O_3$: | 57.7; | 3.1; | 18.3 |
| Found: | 57.7; | 3.1; | 18.0 |

Using the methods of Examples 1 to 3 and starting with the appropriate benzofurans, the following compounds of the invention are prepared.

TABLE I

| Example No. | Intermediate | Product |
|---|---|---|
| 4 | | |

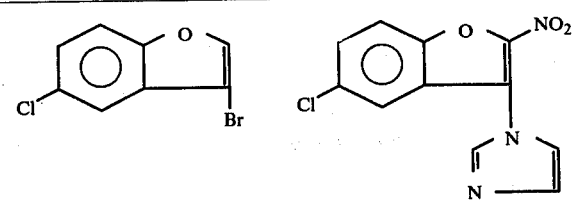

TABLE I-continued

| Example No. | Intermediate | Product |
|---|---|---|
| 5 | 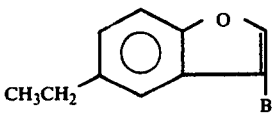 | 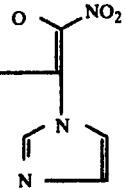 |
| 6 | 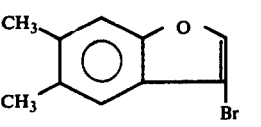 | 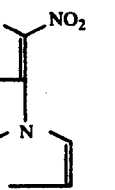 |
| 7 | 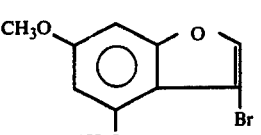 | 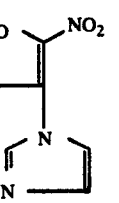 |

The intermediates listed in Table I are conveniently prepared from corresponding substituted salicylaldehydes by methods well known to the art. Thus, the salicylaldehydes are first converted to benzofurans by the method of Burgstahler and Worden (Org. Syn., Vol. 5, page 251). Bromination to the 2,3-dibromo analogs followed by dehydrobromination with a strong base such as potassium hydroxide according to the method of Stoermer and Kahlert (Ber., Vol. 35, page 1633, 1902) afford the desired intermediates.

What is claimed is:

1. A compound of the formula

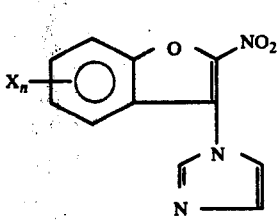

wherein X is halogen, methyl, ethyl or methoxy and n is zero or one, provided that when X is methyl or methoxy n may also be two.

2. The compound 3-(N-imidazolyl)-2-nitrobenzofuran according to claim 1.

3. A method for arresting or inhibiting the growth of microorganisms comprising contacting said microorganisms with a compound according to claim 1 in an amount sufficient to inhibit the growth of said microorganisms.

4. A method according to claim 3 wherein the microorganisms are bacteria.

* * * * *